(12) United States Patent
Saha et al.

(10) Patent No.: US 9,211,415 B2
(45) Date of Patent: Dec. 15, 2015

(54) PHRENIC NERVE STIMULATION DETECTION WITH POSTURE SENSING

(71) Applicant: Cardiac Pacemakers, Inc., St. Paul, MN (US)

(72) Inventors: Sunipa Saha, Shoreview, MN (US); Holly Rockweiler, Minneapolis, MN (US); Aaron R. McCabe, Edina, MN (US); Krzysztof Z. Siejko, Maple Grove, MN (US); John D. Hatlestad, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/191,094

(22) Filed: Feb. 26, 2014

(65) Prior Publication Data

US 2014/0277280 A1 Sep. 18, 2014

Related U.S. Application Data

(60) Provisional application No. 61/779,749, filed on Mar. 13, 2013.

(51) Int. Cl.
*A61N 1/365* (2006.01)
*A61B 5/0205* (2006.01)
(Continued)

(52) U.S. Cl.
CPC .......... *A61N 1/36535* (2013.01); *A61B 5/0205* (2013.01); *A61N 1/3601* (2013.01); *A61N 1/3702* (2013.01); *A61N 1/371* (2013.01)

(58) Field of Classification Search
CPC ......... A61N 1/08; A61N 1/362; A61N 1/365; A61N 1/36514; A61N 1/36535; A61N 1/36542; A61N 1/37; A61N 1/3702; A61N 1/3704; A61N 1/371; A61N 1/3712; A61B 5/1116; A61B 5/0205; A61B 5/08
USPC .................. 607/9, 11, 15, 20, 27, 28
See application file for complete search history.

(56) References Cited

U.S. PATENT DOCUMENTS 7,142,919 B2 11/2006 Hine et al.
7,299,093 B2 11/2007 Zhu et al.
(Continued)

FOREIGN PATENT DOCUMENTS

CN 104321107 A 1/2015
WO WO-2013148053 A1 10/2013

OTHER PUBLICATIONS

"International Application Serial No. PCT/US2013/028315, International Search Report mailed Jul. 11, 2013", 3 pgs.
(Continued)

*Primary Examiner* — Carl H Layno
*Assistant Examiner* — Eugene Wu
(74) *Attorney, Agent, or Firm* — Schwegman Lundberg & Woessner, P.A.

(57) ABSTRACT

A method and a system of phrenic nerve stimulation detection in conjunction with posture sensing is disclosed. In an embodiment, the method may include receiving a trigger for conducting a pace-induced phrenic nerve stimulation (PS) search using the IMD within the patient. On receiving the trigger, the IMD may be used for conducting the PS search. A procedure of conducting the PS search may include measuring a posture of the patient using an implantable posture sensor, searching for PS while the patient is in the measured posture and obtaining a PS result from the PS search for the measured posture. The method may include recording both the PS result and the measured posture in a memory of the IMD.

20 Claims, 14 Drawing Sheets

(51) Int. Cl.
*A61N 1/36* (2006.01)
*A61N 1/37* (2006.01)

(56) References Cited

U.S. PATENT DOCUMENTS

| | | | |
|---|---|---|---|
| 7,354,404 B2 | 4/2008 | Kim et al. | |
| 7,426,412 B1 | 9/2008 | Schecter | |
| 7,477,932 B2 | 1/2009 | Lee et al. | |
| 7,499,751 B2 | 3/2009 | Meyer et al. | |
| 7,636,599 B1 | 12/2009 | Koh et al. | |
| 7,972,276 B1 | 7/2011 | Min | |
| 8,326,418 B2 | 12/2012 | Sommer et al. | |
| 8,326,420 B2 | 12/2012 | Skelton et al. | |
| 8,527,051 B1* | 9/2013 | Hedberg et al. | 607/18 |
| 8,532,774 B1* | 9/2013 | Hedberg et al. | 607/28 |
| 8,626,292 B2 | 1/2014 | Mccabe et al. | |
| 8,634,915 B2 | 1/2014 | Mccabe et al. | |
| 8,958,876 B2 | 2/2015 | Dong et al. | |
| 9,031,651 B2 | 5/2015 | Rockweiler et al. | |
| 2005/0145246 A1 | 7/2005 | Hartley et al. | |
| 2008/0288023 A1* | 11/2008 | John | 607/59 |
| 2009/0043351 A1 | 2/2009 | Sathaye et al. | |
| 2009/0210024 A1 | 8/2009 | M. | |
| 2010/0010590 A1* | 1/2010 | Skelton et al. | 607/62 |
| 2010/0262204 A1 | 10/2010 | Mccabe et al. | |
| 2010/0305637 A1 | 12/2010 | McCabe et al. | |
| 2010/0305638 A1 | 12/2010 | McCabe et al. | |
| 2010/0305647 A1 | 12/2010 | Mccabe et al. | |
| 2011/0152956 A1* | 6/2011 | Hincapie Ordonez et al. | 607/4 |
| 2012/0035685 A1 | 2/2012 | Saha et al. | |
| 2012/0078320 A1 | 3/2012 | Schotzko et al. | |
| 2012/0296388 A1 | 11/2012 | Zhang et al. | |
| 2013/0060298 A1 | 3/2013 | Splett et al. | |
| 2013/0261471 A1 | 10/2013 | Saha et al. | |
| 2013/0261476 A1 | 10/2013 | Rockweiler et al. | |
| 2013/0261688 A1 | 10/2013 | Dong et al. | |
| 2013/0289640 A1* | 10/2013 | Zhang et al. | 607/17 |
| 2014/0005742 A1 | 1/2014 | Mahajan et al. | |
| 2014/0018872 A1 | 1/2014 | Siejko et al. | |
| 2014/0018875 A1 | 1/2014 | Brisben et al. | |
| 2014/0088661 A1 | 3/2014 | Hincapie Ordonez et al. | |
| 2014/0100626 A1 | 4/2014 | Mccabe et al. | |
| 2014/0128933 A1 | 5/2014 | Brooke | |
| 2014/0277244 A1 | 9/2014 | Rockweiler et al. | |

OTHER PUBLICATIONS

"International Application Serial No, PCT/US2013/028315, Written Opinion mailed Jul. 11, 2013", 6 pgs.

* cited by examiner

900

| Position | PS PRESENCE | PS FREQUENCY |
|---|---|---|
| Sitting (X=0 Y=0 Z=0.5) | Yes | Relatively consistent |
| Supine (X=1 Y=0 Z=0) | No | |
| Left Recumbent (X=0 Y=-1 Z=0) | No | |
| Other position X° Y° Z° | Yes | < 10 beats |

902 — Position
904 — PS PRESENCE
906 — PS FREQUENCY

910

Current position: X =0.1, Y=1, Z=0

Left Recumbent Posture

| Visit | LV Tip-Ring | LV Ring-Tip | LV Tip-RV | LV Ring-RV |
|---|---|---|---|---|
| Enroll | 7.5V | NoPS | 4.0V | 5.5V |
| 1MFU | NoPS | NoPS | 6.5V | NoPS |
| 3MFU | 6.5V | NoPS | 5.5V | 7.0V |

FIG. 9B

PHRENIC NERVE STIMULATION DETECTION WITH POSTURE SENSING

CLAIM OF PRIORITY

This application claims the benefit of priority under 35 U.S.C. §119(e) of U.S. Provisional Patent Application Ser. No. 61/779,749, filed on Mar. 13, 2013, which is herein incorporated by reference in its entirety.

TECHNICAL FIELD

This application is related generally to medical devices and, more particularly, to systems, devices and methods that detect pace-induced phrenic nerve stimulation.

BACKGROUND

Implanted pacing systems may be used to pace the heart. When the heart is paced in the left ventricle (LV), for example, there may be unwanted stimulation of the phrenic nerve that causes contraction of the diaphragm. Unintended phrenic nerve activation (an unintended action potential propagated in the phrenic nerve that causes a noticeable diaphragm contraction) is a well-known consequence of left ventricular pacing. The left phrenic nerve, for example, descends on the pericardium to penetrate the left part of the diaphragm. In most people, the left phrenic nerve runs close to the coronary vein targets for LV lead placement. The unintended phrenic nerve activation may cause the diaphragm to undesirably contract. Unintended phrenic nerve activation may feel like hiccups to the patient. Such unintended phrenic nerve activation can occur when the electric field of the LV pacing lead is proximate to the left phrenic nerve and is at a stimulation output that is strong enough to capture the nerve. Unintended phrenic nerve activation may vary from patient to patient. One reason for this variance is that the anatomic location of the phrenic nerve can vary within patients. Additionally, the veins in which the cardiac lead may be placed are not always in the same location with respect to the ventricle and the nearby passing nerve. Also, the selected position in which to place a cardiac lead for a prescribed cardiac therapy may vary.

Although phrenic nerve stimulation is commonly assessed at implant, unintended phrenic nerve activation caused by phrenic nerve capture during pacing may first appear or worsen post-implant for a variety of reasons. Therefore, special office visits after implant may be necessary or desirable to reprogram the device or worse, surgically reposition the lead to avoid phrenic nerve stimulation.

SUMMARY

In an example of a system of phrenic nerve stimulation detection in conjunction with a posture sensing, the system may include an implantable medical device (IMD) for implantation in a patient. The IMD may include a posture sensor, a phrenic nerve stimulation (PS) sensor, a memory, and a controller operably connected to the posture sensor to detect posture and to the PS sensor to detect phrenic nerve stimulation. The controller may be configured to receive a trigger for conducting a PS search and to conduct the PS search in response to the trigger. The PS search conducted by the controller may measure a posture of the patient using the posture sensor, search for PS using the PS sensor while the patient is in the measured posture and obtain a PS result from the PS search for the measured posture, and record in the memory both the PS result and the measured posture.

In an example of a method performed using the IMD within an ambulatory patient, the method may include receiving a trigger for conducting a pace-induced phrenic nerve stimulation (PS) search using the IMD within the ambulatory patient, and conducting the PS search in response to the trigger. Conducting the PS search may include measuring a posture of the ambulatory patient using an implantable posture sensor, searching for PS while the ambulatory patient is in the measured posture and obtaining a PS result from the PS search for the measured posture, and recording both the PS result and the measured posture in a memory of the IMD.

This Summary is an overview of some of the teachings of the present application and is not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 9A-9B illustrate, by way of examples, embodiments of tables to depict PS search results for an ambulatory patient.

DETAILED DESCRIPTION

Figure 1:
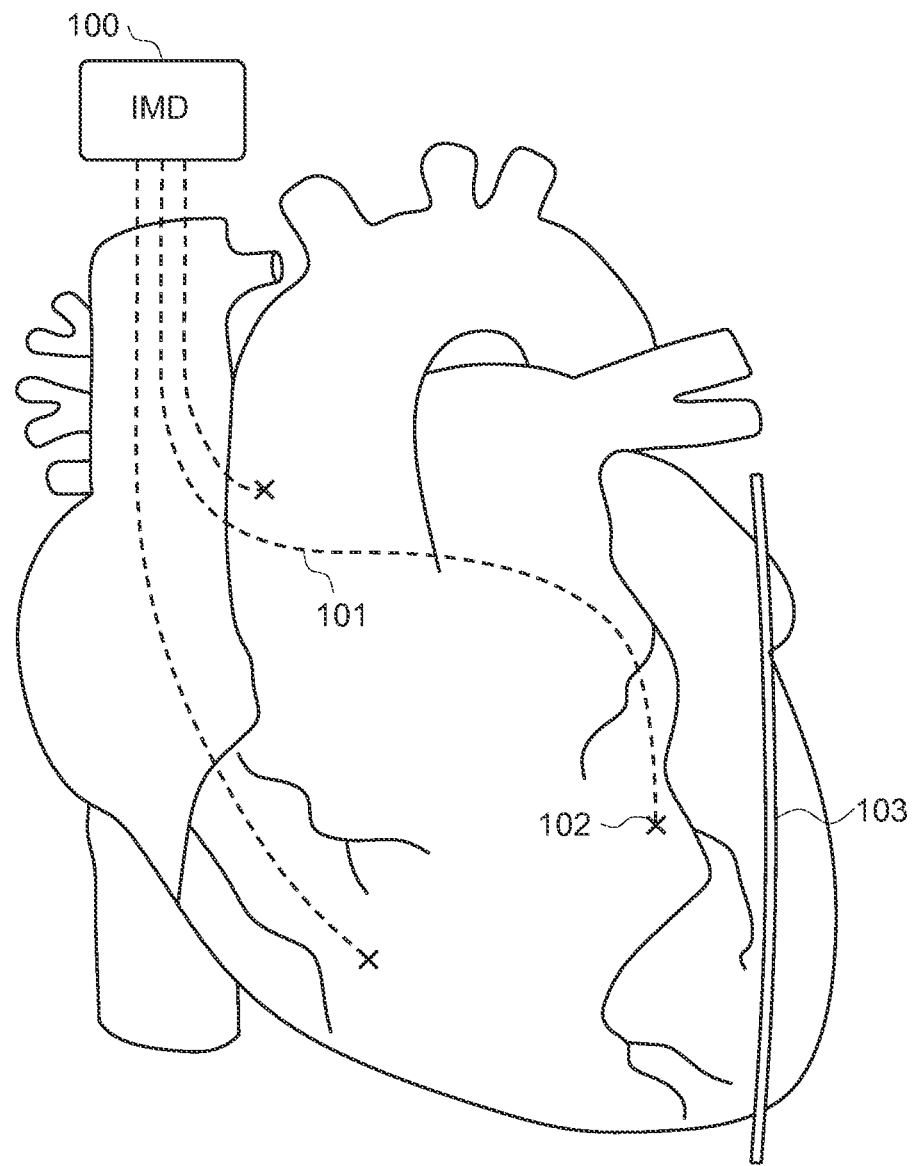
FIG. 1 illustrates, by way of example, an embodiment of an implantable medical device (IMD) configured to deliver myocardial stimulation therapy to a patient.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an," "one," or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Some embodiments, for example, implement an automatic detection algorithm for detecting unintended phrenic nerve activation (also referred to herein as pace-induced phrenic nerve stimulation or as phrenic nerve stimulation "PS"). According to various embodiments, the PS detection algorithm(s) can be used in a clinical setting such as during implant procedures or in patient follow-up visits, or an ambulatory setting such as in a patient's home, or in both the clinical and ambulatory setting. The PS detection algorithm(s) may lessen or alleviate the burden of the patients and clinical staff to adequately address the problems of PS. For example, the ability to accurately and/or automatically detect PS may reduce prolonged discomfort for patients experiencing PS during myocardial stimulation therapies, and may reduce the burden on hospitals and staff for testing and reprogramming devices.

As PS may be an unintended side effect of some cardiac pacing therapies, a brief discussion of myocardial stimulation and the phrenic nerve is provided below.

Myocardial Stimulation and the Phrenic Nerve

A myocardial stimulation therapy may deliver a cardiac therapy using electrical stimulation of the myocardium. Some examples of myocardial stimulation therapies, and devices for performing the therapies, are provided below. A pacemaker is a device which paces the heart with timed pacing pulses, most commonly for the treatment of bradycardia where the ventricular rate is too slow. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and then to the ventricular myocardium to provide a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure. Heart failure refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. A CRT example applies stimulation pulses to both ventricles, either simultaneously or separated by a specified biventricular offset interval, and after a specified atrio-ventricular delay interval with respect to the detection of an intrinsic atrial contraction or delivery of an atrial pace.

CRT can be beneficial in reducing the deleterious ventricular remodeling which can occur in post-myocardial infarction (MI) and heart failure patients, which appears to occur as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions may be the trigger for ventricular remodeling. Pacing one or more sites may cause a more coordinated contraction, by providing pre-excitation of myocardial regions which would otherwise be activated later during systole and experience increased wall stress. The pre-excitation of the remodeled region relative to other regions unloads the region from mechanical stress and allows reversal or prevention of remodeling to occur.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected. ATP may be referred to as overdrive pacing. Other overdrive pacing therapies exist, such as intermittent pacing therapy (IPT), which may also be referred to as a conditioning therapy.

Both a right phrenic nerve and a left phrenic nerve pass near the heart and innervate the diaphragm below the heart. Pace-induced phrenic nerve stimulation, also referred to herein as PS, may be observed with various forms of pacing. PS may be observed particularly with LV pacing because of the close proximity of the LV pacing site to the left phrenic nerve. PS is a common side effect of CRT. Cardiac stimulation at other locations of the heart may result in PS in either the left or right phrenic nerve. The present subject matter is not limited to PS of the left phrenic nerve during LV pacing, but may be implemented to appropriately address PS in either the left or right phrenic nerve caused by myocardial stimulation or other stimulation.

During a cardiac lead implant procedure such as an LV lead implant, for example, a physician may test for the presence of phrenic nerve stimulations (PS) for different pacing configurations and different stimulation parameters. Examples of pacing configurations can include, but are not limited to, LV bipolar, LV to can, and LV to right ventricle (RV) and examples of stimulation parameters can include an amplitude (e.g. voltage) and pulse width of stimulation pulses. Accordingly, the physician can program the IMD to deliver the cardiac therapy using only those pacing configurations or the stimulation parameters of the cardiac therapy that inhibit the unintended PS.

A PS threshold represents a smallest pacing parameter, such as a pacing amplitude for an LV pace, at which it can be determined that PS occurs with the pace. Thus, for example, PS is determined to generally occur when the pacing amplitude is equal to or greater than the PS threshold. PS may not occur for every pace equal to or greater than the PS threshold.

Various studies further suggest that PS threshold voltage levels are dependent on patient posture. For example, patients have reported that PS may appear or disappear in certain body postures after surgery. The posture of the patient may change the PS threshold. A PS threshold level associated with a first posture of a patient can be different from a PS threshold level associated with a second posture of the patient. As a result, when the patient is in an ambulatory environment, a posture change (i.e., moving from the first posture to the second posture) may reduce the PS threshold level and result in unintended stimulations of the phrenic nerve. The patient may further experience that PS may appear or disappear in certain body postures. Some embodiments use an activity sensor to provide context, and some embodiments use a timer to determine a time of day to provide context. Some embodiments allow the device to store posture, activity, time of day and the like with the detected PS data to determine the context when the PS is observed.

FIG. 1 illustrates, by way of example, an embodiment of an implantable medical device (IMD) 100 configured to deliver the myocardial stimulation therapy to a patient. The illustrated IMD 100 can be programmed to deliver the myocardial stimulation therapy or other aforementioned therapies using leads represented by the dotted lines and electrodes represented by "X" fed into the heart. FIG. 1 illustrates, by way of example and not limitation, electrodes configured to pace the right atrium, the right ventricle and the left ventricle. The lead 101 passing through the coronary sinus of the heart includes a left ventricular electrode 102, or electrodes, for use to stimulate the left ventricle at a stimulation site. FIG. 1 also indicates that the left ventricular electrode 102 of the lead 101 is relatively close to the left phrenic nerve 103 of the patient. PS may occur for certain configurations of pacing vectors or electrode placement. Various examples of the present subject matter may be used in procedures for using PS sensor(s) to detect PS. By way of example and not limitation, a PS sensor may include a sensor to detect motion caused by the diaphragm contraction. Some examples can use an accelerometer to detect PS. Other examples of sensors that may be used to detect PS can include, but are not limited to, an acoustic sensor, a respiration sensor, an impedance sensor, a neural sensor on the phrenic nerve, or an electromyogram (EMG) sensor for sensing signals indicative of diaphragm contraction.

A change in posture can change the proximity between the lead 101 and the left phrenic nerve 103. If the change in posture causes the lead 101 and left phrenic nerve 103 to move within the electrical field of stimulation, for example, there may be a reduction in the PS threshold which may cause unintended PS. Various embodiments use one or more posture sensors to indicate a posture of the patient. A change in the posture of the patient can cause variations in the PS threshold voltage levels for the patient. Thus, an amplitude for a myocardial pace may not induce PS when the patient is in a first posture, but the same amplitude of the myocardial pace may induce PS when the same patient is in a second posture. Stated another way, the PS threshold level can have a first threshold value when the patient is at first posture and the PS threshold level can have a second threshold value when the patient is at a second posture. The posture sensor(s) may be used to provide contextual information. This contextual information may be recorded with detected PS events, and used to determine the posture(s) in which PS occurs. In some embodiments, this information may be communicated to the clinician, and used by the clinician to program the cardiac stimulation therapy to avoid PS when the patient is in the corresponding posture for which the PS was previously found to occur. In some embodiments, this information may be used to automatically adjust the programmed cardiac stimulation therapy to avoid PS when the patient is in the corresponding posture.

Figure 2:
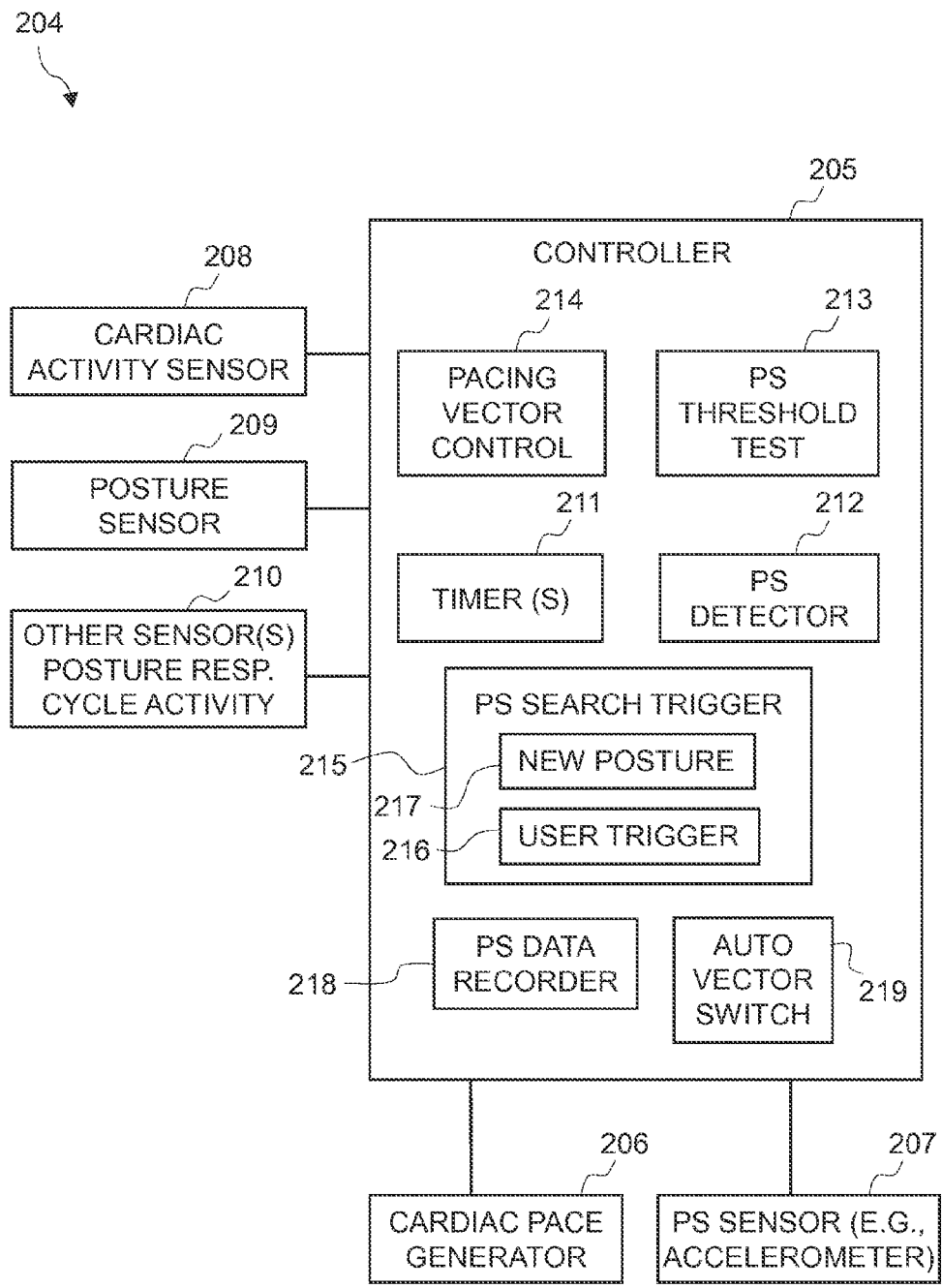
FIG. 2 illustrates, by way of example, an embodiment of the IMD.

FIG. 2 illustrates, by way of example, an embodiment of the IMD. The IMD 204 may be used to deliver myocardial stimulations to the patient and to detect PS caused by the myocardial stimulations. The IMD 204 includes a controller 205, a cardiac pace generator 206, a PS sensor 207, a cardiac activity sensor 208 and a posture sensor 209. The same sensor (e.g. accelerometer) may be used to perform the functions of any two or all of the posture sensor, the cardiac activity sensor, or the PS sensor. In an example, the IMD 204 can include one or more other sensors 210 such as, by way of example and not limitation, a sensor used for detecting respiration or a respiration cycle, or a sensor used for detecting hemodynamic performance of the heart or other sensor useful for therapy delivery or for diagnostic purposes. In an example, the IMD 204 can be programmed to implement a cardiac pacing algorithm, in which the controller 205 receives sensed cardiac activity from the cardiac activity sensor 208, uses timer(s) 211, such as a cardiac pacing timer, to determine a pace time for delivering a cardiac pace or other myocardial stimulation pulse, and controls the cardiac pace generator 206 to deliver the cardiac pace at the desired time.

The controller 205 includes a PS detector 212 that can cooperate with the PS sensor 207 to discriminate if a signal from the PS sensor 207 is indicative of PS events. A PS event can be determined from a PS sensor signal as a time in which PS occurs. In an example, the PS detection may occur in the same IMD that is providing the myocardial stimulation, or may occur in another IMD. In an example, an accelerometer can be used to provide the PS detection and can be positioned near the diaphragm or near the portion of the diaphragm innervated by the phrenic nerve or near the apex of the heart, which may improve the signal to noise characteristics of the signal sensed by the PS sensor 207.

In an example, the IMD 204 can be configured with a PS threshold test module 213 that can be used to perform PS threshold test(s). The PS threshold test can be configured to deliver myocardial stimulation using different stimulation parameters. The PS threshold tests can be configured to determine the myocardial stimulation parameters that cause or that may cause PS, or determine the myocardial stimulation parameters that do not cause PS. The physical position of the stimulation electrode or electrodes used to deliver the myocardial stimulation may be adjusted in an attempt to avoid PS that can occur during an implantation procedure. In an example, a physician may physically move the electrode. Some embodiments may provide electronic repositioning by selecting a set of stimulation electrodes from a larger set of potential stimulation electrodes.

In an example, the pacing vector between or among stimulation electrodes may be modified in an attempt to avoid PS. The controller in some IMD embodiments may include a pacing vector control module 214 used to change the pacing vectors. The pacing vector control module 214 may be implemented under the control of a clinician through an external programmer, or may be implemented autonomously by the IMD 204 in the ambulatory setting. In an example, the controller 205 can be configured to include a PS search trigger module 215 that can trigger the IMD 204 to conduct the PS search such as to detect the presence of the unintended PS for example, due to the change in the posture of the patient. For example, a posture change may trigger a PS search. The trigger can be initiated by users such as the physician or the patient as generally illustrated by the user trigger module 216. The user trigger module 216 can be configured with defined events or conditions so that the PS search trigger module 215 can trigger the IMD 204 to conduct the PS search on occurrence of such events or conditions. The PS search trigger module 215 may initiate a PS search on detection of a new posture 217, or relatively new posture, of the patient. For example, the posture sensor may detect a posture of the patient and the controller 205 may access a PS data recorder 218 to determine whether the IMD 204 has PS or other configuration data for the detected posture of the patient. If the IMD 204 has PS or other configuration data, the IMD 204 may determine whether this data should be updated because of, for example, the age of the data, changes in the therapy, changes in the device, or changes in the condition of the patient. In an example, the IMD 204 may also determine whether the data should be updated because the conditions under which the data was previously collected. For example, the data may have previously been collected under noisy conditions. Thus, for example, the PS search trigger module 215 can trigger the PS search on determining that the detected posture is not recorded in the PS data recorder 218 and the detected posture is a new posture 217 of the patient. In an example, the controller 205 can be configured to store PS related information such as a presence or absence of the PS for a particular posture, therapy, pacing vector and the other parameters in a PS data recorder 218.

The IMD 204 can be configured to operatively couple to an auto vector switch 219 that can be configured to switch the delivery of the myocardial stimulation therapy from a first pacing vector configuration to a second pacing vector configuration to avoid the presence of the PS at a particular posture of the patient. The auto vector switch 219 may access the PS data recorder 218 to extract a suitable pacing vector for a particular therapy to avoid the PS that can occur when the patient changes his/her posture from the first posture to the second posture. The PS data recorder 218 can include a priority list of pacing vectors for the particular posture of the patient. For example, the priority list can indicate a bipolar pacing vector configuration at a higher priority level and a unipolar pacing vector configuration at a lower priority level to avoid the PS for a particular type of myocardial stimulation therapy at a particular posture of the patient. Accordingly, the auto vector switch 219 can enable the controller 205 to switch delivery of the myocardial stimulation therapy from a current pacing vector configuration to a pacing vector configuration having the higher priority level when the posture of the patient changes.

Figure 3:
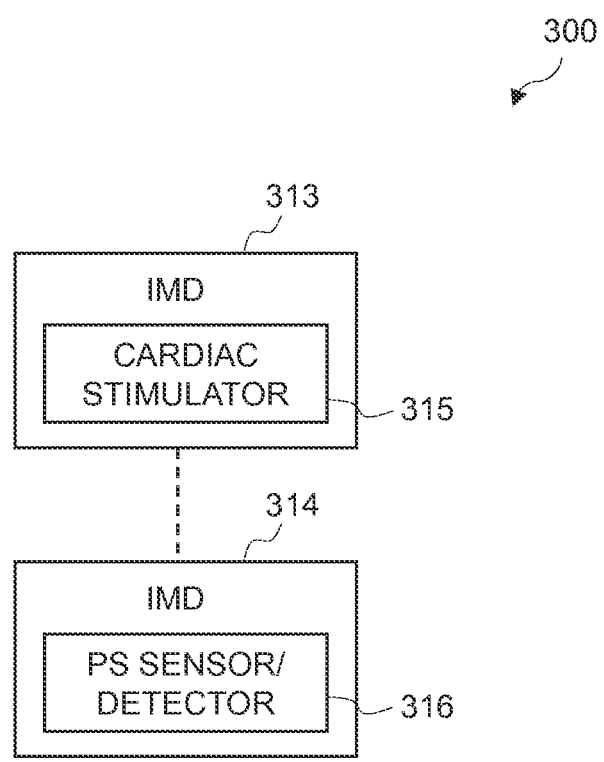
FIG. 3 illustrates, by way of example, an embodiment of a system that includes two or more IMDs.

FIG. 3 illustrates an embodiment of a system 300 that includes two or more IMDs such as a first IMD 313 and a second IMD 314. By way of example and not limitation, the first IMD 313 may be a pacemaker or other cardiac rhythm management device. The second IMD 314 in the illustrated system 300 can include a PS detector/sensor 315 that can be used to detect PS that may be caused by the myocardial stimulation pulses delivered from the first IMD 313. In an example, the IMDs 313, 314 may communicate with each other over a wired connection. In an example, the IMDs 313, 314 may communicate with each other over a wireless connection such as by using an ultrasound or radiofrequency (RF) or any other wireless technology. IMD 313, IMD 314, or both IMDs 313 and 314 may include a posture sensor.

The PS sensor(s) used for detecting PS may be implanted or may be external. The algorithms for processing the sensed signals to detect PS may be performed within one or more of the IMD(s) 313 and 314 and/or may be performed in external devices. By way of example, some examples may use implantable sensor(s) and use external device(s) to process the sensed signals to detect PS. The monitoring of the patient for PS may be performed in a clinical setting or in an ambulatory setting. This monitoring, regardless of whether it is performed in the clinical setting or an ambulatory setting, may be performed using implanted PS detectors such as illustrated in FIGS. 2-3, for example, and/or may be performed using external PS detectors. The patient can be monitored for a change in the posture of the patient and the PS sensor/detector 316 can detect the presence of the PS upon a change in the posture of the patient. Accordingly, the PS sensor/detector 316 can communicate the presence or absence of the PS on the change in the postures of the patient so that the IMD 313 can be configured to avoid PS on the change in the posture of the patient.

Figure 4:
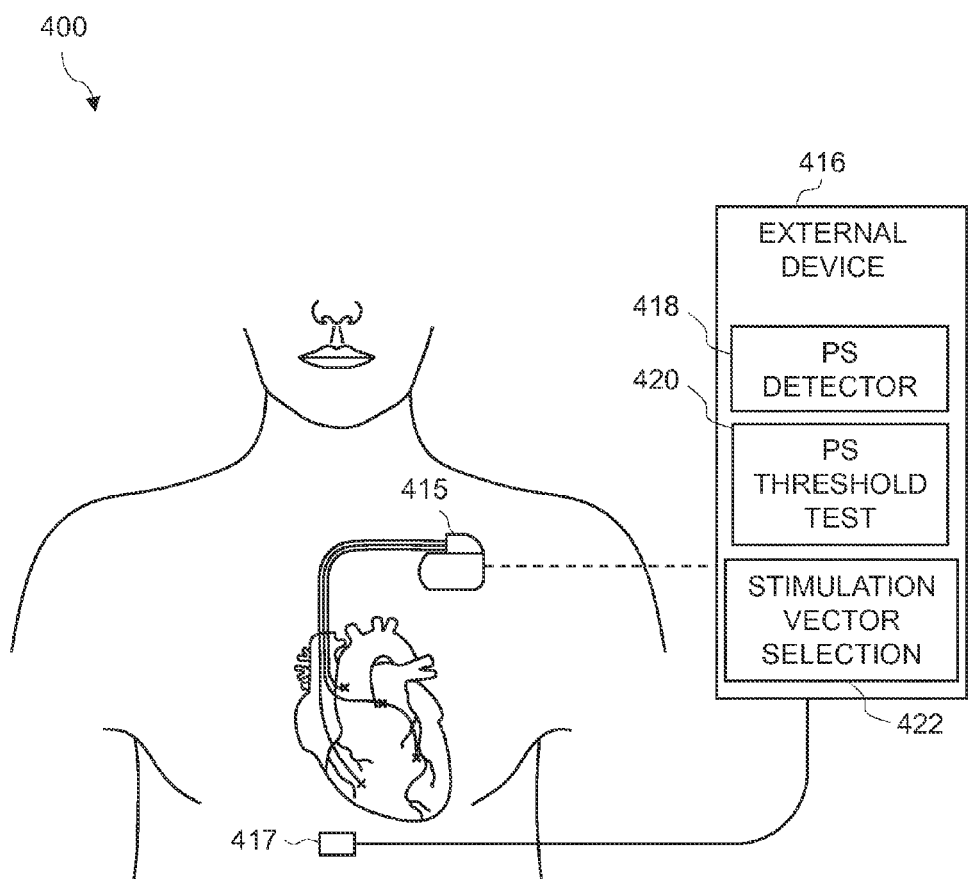
FIG. 4 illustrates, by way of example, an embodiment of a system including an external phrenic nerve stimulation (PS) detector to detect PS.

FIG. 4 illustrates an example of a system 400 that includes an IMD 415 such as a cardiac rhythm management device, an external device 416, and an external PS sensor 417. The system 400 may be implemented in a clinical setting such as by the clinician who uses the external device 416 as a programmer to program the IMD 415; or the system 400 may be implemented by the patient in an ambulatory setting to occasionally check if the myocardial stimulation is causing PS. The external PS sensor 417 may be integrated with the external device 416, such that the PS may be sensed by holding or otherwise positioning the external device 416 next to the patient (e.g. externally positioned near the diaphragm or near the apex of the heart).

In various embodiments, the external device 416 includes a PS detector 418 that cooperates with the PS sensor 417 to discriminate if a signal from the PS sensor 417 indicates the presence of PS events. In various embodiments, the external device 416 includes a PS threshold test module 420 used to perform PS threshold test(s). The PS threshold test module 420 can be configured to control the IMD 415 to deliver myocardial stimulation using different stimulation parameters. The PS threshold test module 420 can be configured to determine the myocardial stimulation parameters that cause or that may cause PS, or myocardial stimulation parameters that do not cause PS. In an example, the physical position of the stimulation electrode or electrodes used to deliver the myocardial stimulation may be adjusted in an attempt to avoid PS. In various embodiments, the external device 416 includes a stimulation vector selection module 422 that can select pacing vector between or among stimulation electrodes, which may be modified in an attempt to avoid PS. Depending on the presence of PS in the signal delivered by the PS sensor 417 for a particular posture of the patient, the stimulation vector selection module 422 can select an appropriate pacing vector of the stimulation electrodes so that the patient may not experience any unintended PS that can be caused by the myocardial stimulation delivered to the patient during the particular posture of the patient.

Figure 5:
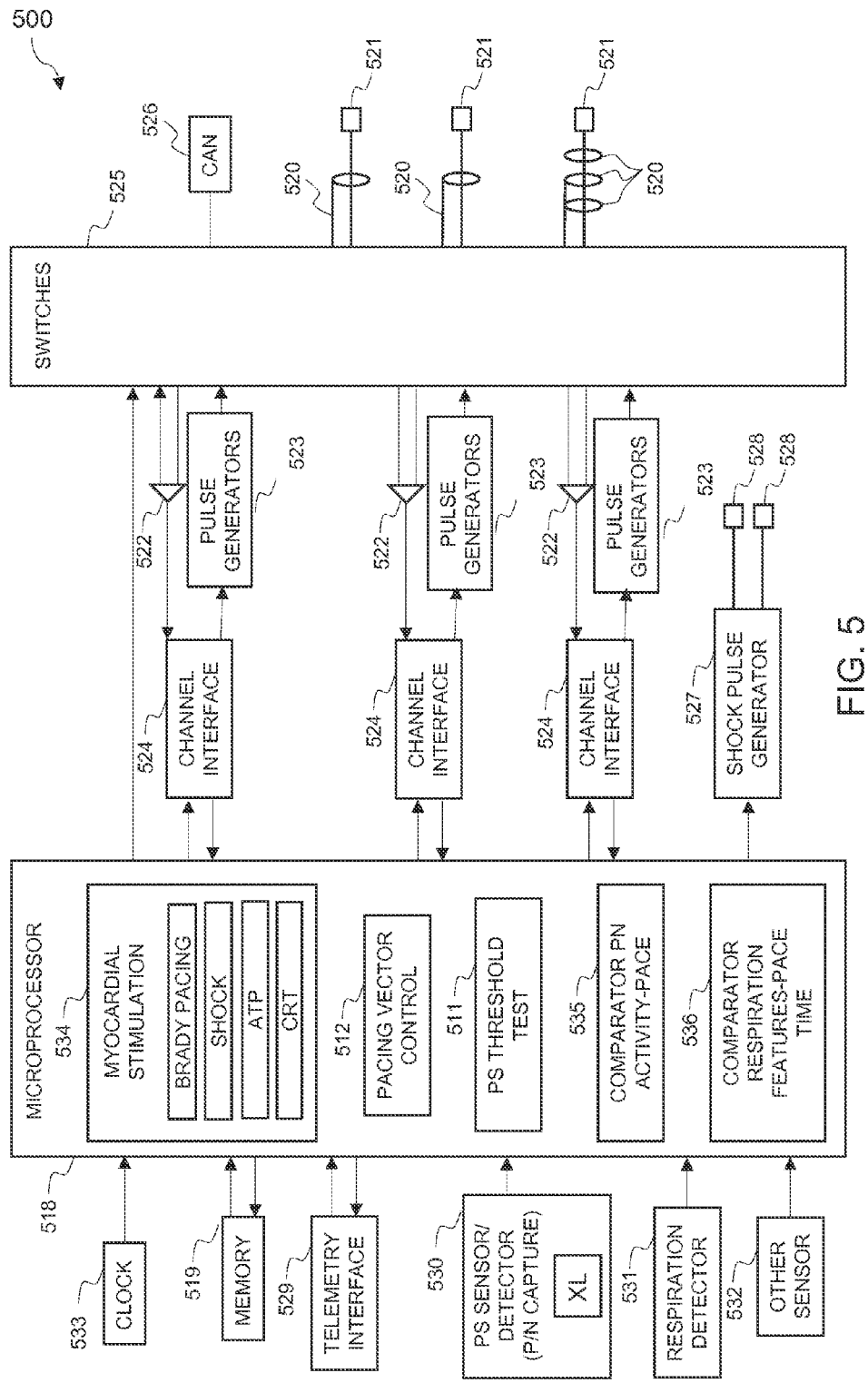
FIG. 5 illustrates, by way of example, a system diagram of an embodiment of a microprocessor-based implantable medical device.

FIG. 5 illustrates a system diagram of an example of a microprocessor-based implantable device 500. The controller of the device 500 is a microprocessor 518 which communicates with a memory 519 via a bidirectional data bus. The controller can be implemented by other types of logic circuitry (e.g., discrete components or programmable logic arrays) using a state machine type of design. As used herein, the term "circuitry" should be taken to refer to either discrete logic circuitry, firmware, or to the programming of a microprocessor. The microprocessor 518 can be configured to operate in accordance with the timing associated with a clock 533 such as to deliver the stimulations to one or more bodily tissues of the patient.

As illustrated in FIG. 5, three examples of sensing and pacing channels comprising leads with ring electrodes 520 and tip electrodes 521, sensing amplifiers 522, pulse generators 523, and channel interfaces 524 can be utilized to deliver a particular therapy as controlled using the microprocessor 518. One of the illustrated leads includes multiple ring electrodes 520, such as may be used in a multi-polar lead. An example of a multipolar lead is a left ventricle quadripolar lead. Each channel thus includes a pacing channel made up of the pulse generator connected to the electrode and a sensing channel made up of the sense amplifier connected to the electrode. The channel interfaces 524 communicate bi-directionally with the microprocessor 518, and each interface may include analog-to-digital converters for digitizing sensing signal inputs from the sensing amplifiers 522 and registers that can be written to by the microprocessor 518 in order to output pacing pulses, change the pacing pulse amplitude, and adjust the gain and threshold values for the sensing amplifiers. The sensing circuitry of the pacemaker detects intrinsic chamber activity, termed either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each lead are connected via conductors within the lead to a switching network 525 controlled by the microprocessor 518. The switching network 525 is used to switch the electrodes to the input of a sense amplifier 522 in order to detect intrinsic cardiac activity and to the output of a pulse generator in order to deliver a pacing pulse. The switching network 525 also enables the device to sense or pace either in a bipolar mode using both the ring and tip electrodes of a lead or in unipolar or an extended bipolar mode using only one of the electrodes of the lead with the device housing (can) 526 or an electrode on another lead serving as a return electrode. In an example, a shock pulse generator 527 may be interfaced to the controller, in addition or alternative to other stimulation channels, for delivering a defibrillation shock via a pair of shock electrodes 528 to the atria or ventricles upon detection of a shockable tachyarrhythmia. In addition, a can electrode 526 may also be used to deliver shocks. The figure illustrates a telemetry interface 529 connected to the microprocessor, which can be used to communicate with an external device.

As illustrated in FIG. 5, the system 500 can include a PS sensor/detector 530 used to detect PS by myocardial stimulation at a particular posture of the patient. In an example, the PS sensor/detector 530 includes an accelerometer (XL) that can detect accelerations due to characteristic motions of the body, heart, and lungs in the particular posture of the patient. This can cause the XL to generate a time domain acceleration signal that can be stored in the memory 519 such as for determining the detection of unintended PS at the particular posture of the patient. According to various embodiments, the PS sensor/detector 530 can include, but is not limited to, an acoustic sensor, a respiration sensor, an impedance sensor, a neural sensor on the phrenic nerve, or electrodes to sense electromyogram signals indicative of diaphragm contraction. Various embodiments use more than one detector to provide a composite signal that indicates phrenic nerve capture. The use of more than one detector may enhance the confidence in detecting PS events. Various embodiments can also include a respiration detector 531 and/or other sensor(s) 532 that may be used to provide contextual information like activity and posture.

According to various examples, the illustrated microprocessor 518 can be configured to include various myocardial stimulation therapy modules 534 such as to treat one or more cardiac disorders associated with the patient. Examples of myocardial stimulation therapy modules 534 can include bradycardia pacing therapies, anti-tachycardia shock therapies such as cardioversion or defibrillation therapies, anti-tachycardia pacing therapies (ATP), cardiac resynchronization therapies (CRT), and the other therapies that can provide relief to the patient from the one or more cardiac disorders. As illustrated, the controller 518 may also include a comparator 535 to compare a time when phrenic nerve activity is detected to a pace time to determine that phrenic nerve activity is attributed to the pace, and/or may include a comparator 536 to compare respiration features to the pace time for use in detecting PS. The microprocessor 518 may include instructions for performing a PS threshold test 511 and a pacing vector control process 512, similar to the respective PS threshold test 214 and the pacing vector control module 214 of FIG. 2.

In an example, the microprocessor 518 can be configured to receive a trigger for conducting a PS search. The microprocessor 518 can be configured to, upon receiving the trigger, initiate the PS search and measure a posture of the patient using the posture sensor. The microprocessor 518 can be configured to use the PS sensor 530 to determine if PS is present at the corresponding posture of the patient. The microprocessor 518 may be configured to control the pacing algorithms used in delivering the myocardial stimulation therapies to avoid PS for the posture. The microprocessor 518 may be configured to conduct PS searches and store PS search results in the memory 519 along with the corresponding measured posture of the patient. This may be communicated out to an external device for communication to a clinician.

Figure 6:
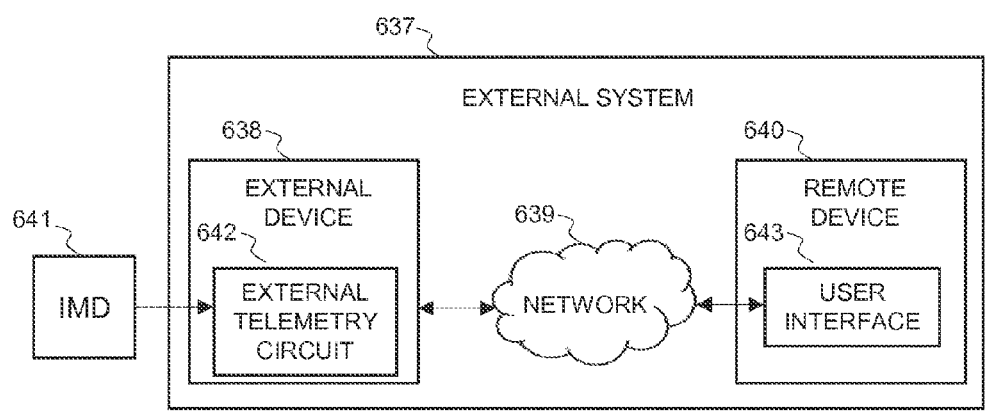
FIG. 6 illustrates, by way of example, an embodiment of a block diagram of an external system configured to remotely detect PS.

FIG. 6 illustrates, by way of example, an embodiment of a block diagram of an external system 637 configured to remotely detect PS. For example, the external system 637 can be used to remotely program the IMD 641 in an ambulatory patient, or to remotely obtain detected PS search results from the ambulatory patient, or to remotely retrieve sensed data from the IMD 641 in the ambulatory patient for analysis of the sensed data to obtain the PS search results in a remote location from the ambulatory patient. The external system 637 can be a programmer or can be a portion of a patient management system. As illustrated, the external system 637 can include an external device 638, a telecommunication network 639, and a remote device 640. The external device 638 is placed within the vicinity of the IMD 641 and includes an external telemetry system 642 to communicate with the IMD 641. The remote device(s) 640 is in one or more remote locations and is operatively coupled to the external device 638 through the telecommunication network 639. The remote device 640 can enable the physician or other caregiver to monitor and treat the patient from a distant location and/or allow access to various treatment resources from the one or more remote locations. The illustrated remote device includes a user interface 643 such as to provide the patient or physician a feedback indicative of patient discomfort.

Figure 8:
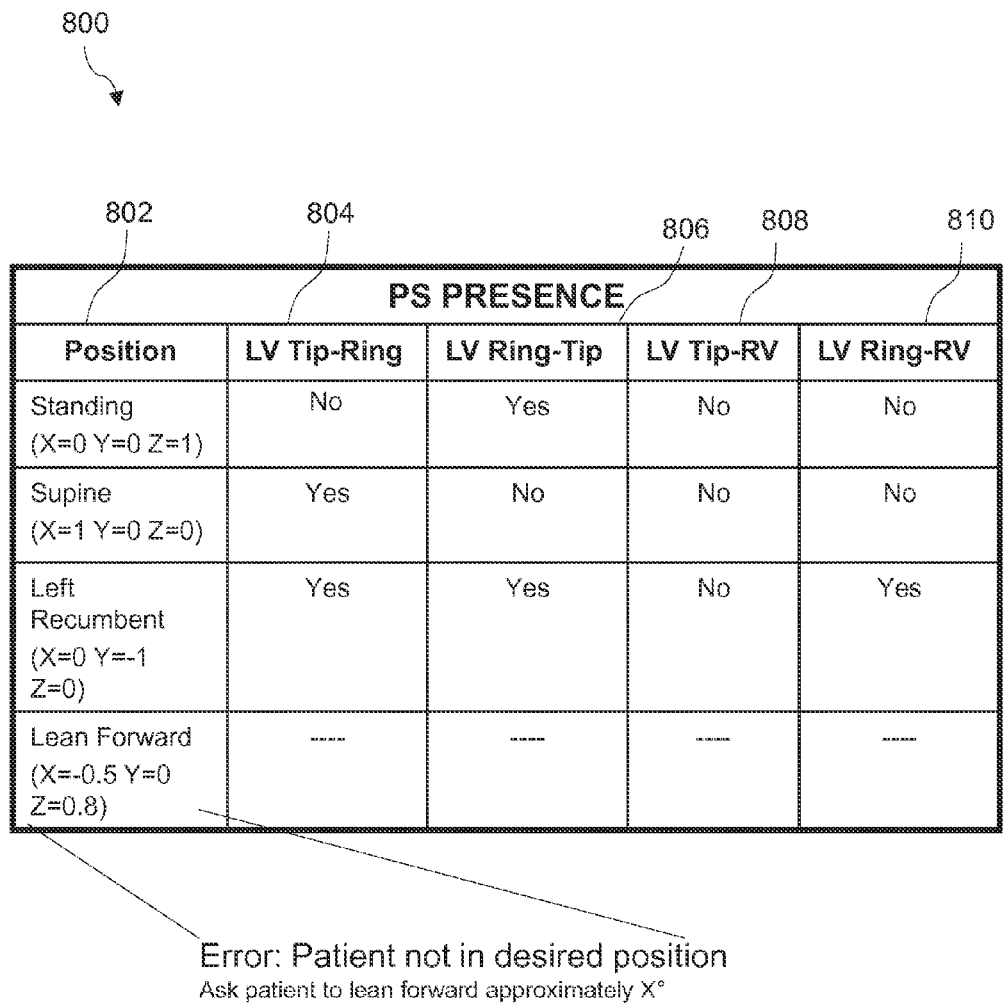
FIG. 8 illustrates, by way of example, an embodiment of a table listing results of a PS search algorithm configured to search for PS at different postures of the patient.

In an example, the IMD 641 can be configured to conduct a plurality of PS searches for one or more postures of the patient. The PS searches may be used to identify a posture of the patient at which the patient experiences the PS. The IMD 641 can be configured to store the PS search results for one or more measured patient postures in the memory and communicate the PS search results to the external device 638 via the external telemetry circuit 642. The remote device 640 may enable the users such as the physicians or the patients to access the PS search results for the measured patient posture(s) through the user interface 643. For example, the PS search results may be displayed to the users in a form of a table such as a table 800 or table 900 as illustrated in FIG. 8 and FIG. 9. According to various embodiments, various processes may be implemented using hardware, firmware, and/or software within the devices and systems discussed above for use in posture detection and PS detection for the corresponding posture and determining corrective actions to avoid the occurrence of the PS corresponding to the posture of the patient. These processes may be, but do not have to be, integrated within the same system.

Figure 7A:
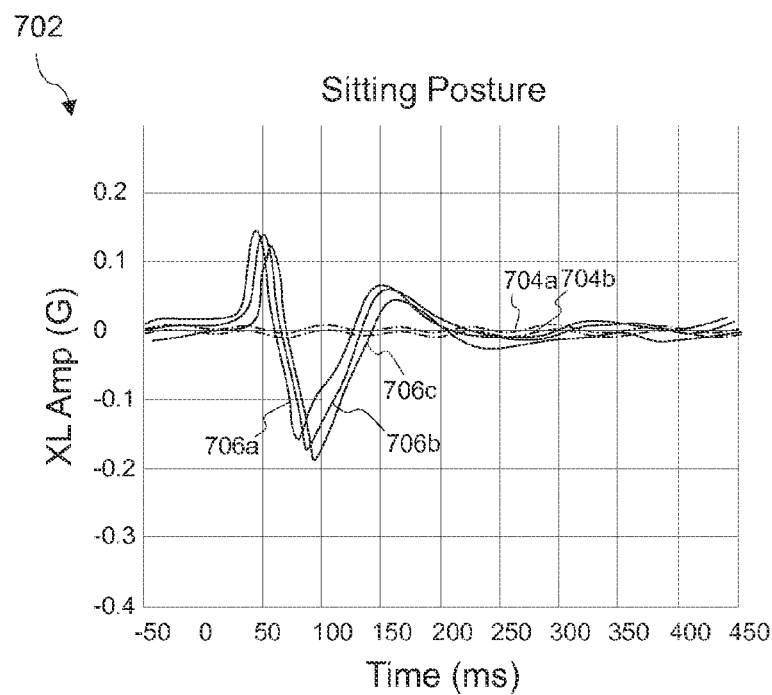
FIGS. 7A-7C illustrate, by way of example, a sample of signals generated from a PS sensor at different postures of the patient.
Figure 7B:
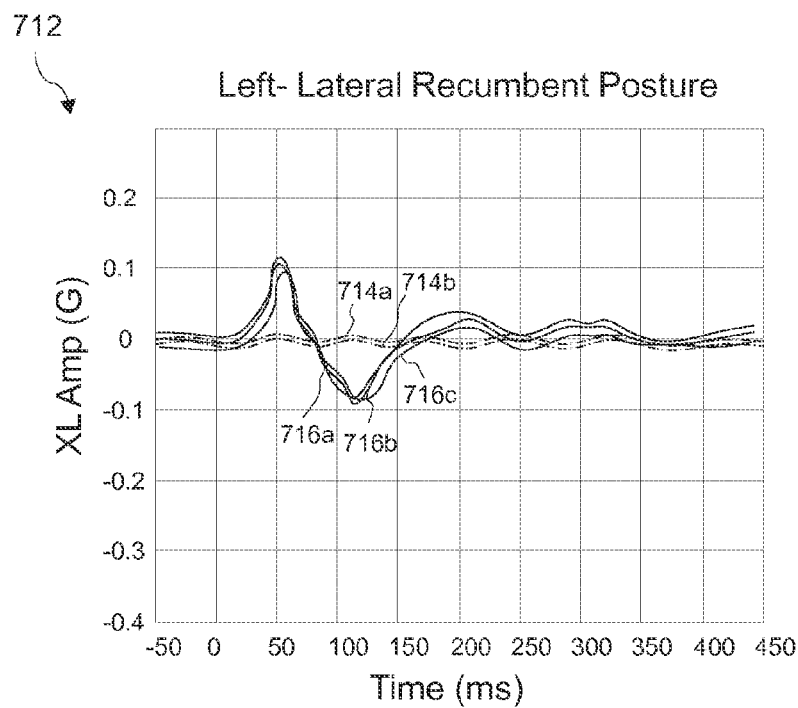
Figure 7C:
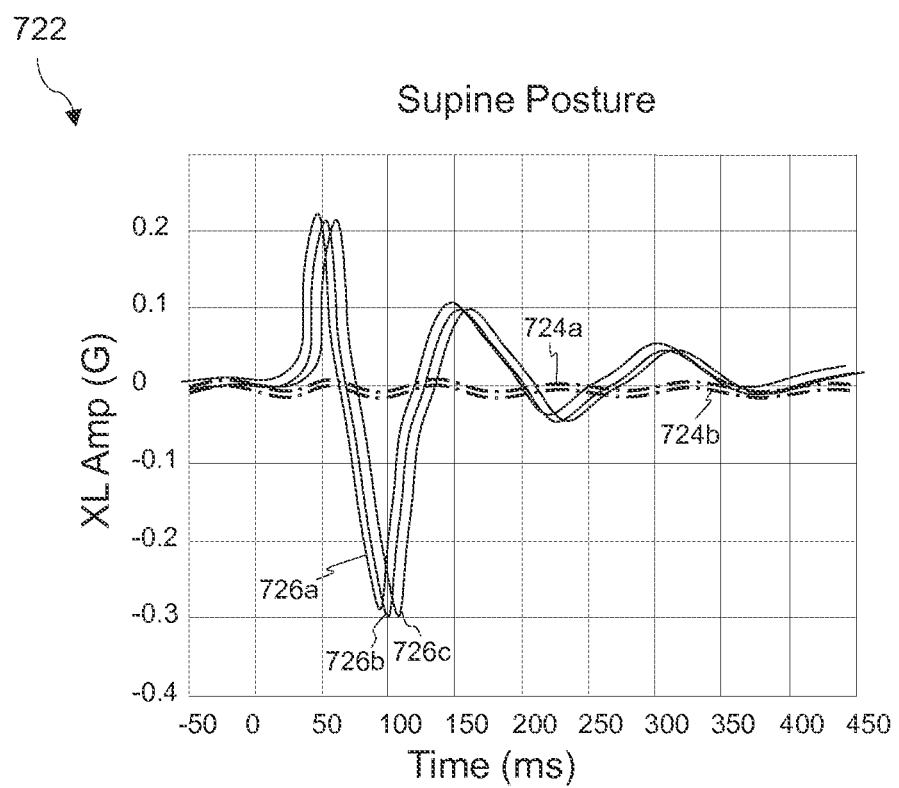

FIGS. 7A-7C illustrate a sample of signals generated from the PS sensor at different postures of the patient. The PS sensor can be a 3-axis accelerometer sensor. By way of example, an amplitude of the accelerometer signal is evaluated to determine PS. For example, amplitudes greater than a threshold amplitude may be used to detect a PS event at the particular posture of the patient, and amplitudes lower than the threshold amplitude may be used to determine that a PS event did not occur FIG. 7A illustrates an example of a sample of accelerometer signals 702 gated/aligned by the LV pace when the patient is at a sitting posture. Patterns 704*a* and a 704*b* may indicate an absence of PS, and patterns 706*a*, 706*b* and 706*c* may indicate a presence of PS. FIG. 7B illustrates an example of a sample of accelerometer signals 712 when the patient is at a left-lateral recumbent posture. Patterns 714*a* and a 714*b* may indicate an absence of the PS, and patterns 716*a*, 716*b* and 716*c* may indicate a presence of the PS. FIG. 7C illustrates an example of a sample of accelerometer signals 722 when the patient is at a supine posture. Patterns 724*a* and 724*b* may indicate an absence of the PS, and patterns 726*a*, 726*b* and 726*c* may indicate a presence of the unintended PS. The patterns illustrated in FIGS. 7A-7C demonstrate similar morphological features across various postures over time for the patient. The methods and systems disclosed herein can extract the similar morphological features from the accelerometer signals of different postures of the patient and utilize the extracted morphological features to classify whether myocardial stimulation is causing PS.

FIG. 8 illustrates an embodiment of a table 800 listing results of a PS search algorithm configured to search for PS at different postures of the patient. The PS search algorithm may be executed upon receiving a request from the physician for example. In some embodiments, the physician request may be made if the patient is in the clinic. In some embodiments, the patient is ambulatory (out of the clinic). In some embodiments, the PS search algorithm may be executed automatically, either at regular or non-regular intervals, depending on the programming parameters of the IMD. In an example, the PS search algorithm can be initiated by an ambulatory patient away from the clinical setting to record the results of the PS search algorithm in an absence of the physician. The PS search algorithm enables the physician to identify specific postures of the patient and identify if PS is present in those postures. A physician can use this information to program the IMD to avoid PS for these postures. In an example, the table 800 illustrated in FIG. 8 may be displayed to the physician or to the patient using an interface such as the user interface 643 of FIG. 6. Table 800 is one example for organizing a display of some PS search results. Additional or fewer PS results may be recorded for additional or fewer pacing vector and/or additional or fewer patient positions. As illustrated in FIG. 8, the table 800 includes a plurality of posture positions of the patient. The posture of the patient can be determined using the posture sensors such as the accelerometer sensor. The illustrated table includes X, Y and Z values for a three-axis accelerometer. Posture information is stored and a PS search routine may be implemented to search for PS among the potential pacing configurations while the patient remains in the posture.

In an example, the table 800 indicates the searched pacing vector configurations such as LV Tip-Ring, LV Ring-Tip, LV Tip-RV, and LV Ring-RV for the LV pacing lead of the IMD. As shown in a column 802 of the table 800, by way of example, the PS search algorithm can be configured to search for PS in each of the pacing vector configurations in the standing posture, the supine posture and the left recumbent posture of the patient. These postures for which a PS search is conducted may be recorded in the table, as illustrated by column 802. The table 800 includes results of the PS search performed using the PS search algorithm. A "NO" may indicate that PS is not present for the combination of the pacing vector configuration and the position, and a "YES" may indicate that PS is present for the corresponding combination of the pacing vector configuration and the position. This table may be reviewed by the physician so that the physician can appropriately program the IMD to provide effective pacing without PS. For example, in addition to a Position column for recording patient posture, the table may include columns to represent available pacing configurations, such as the LV TIP-Ring column 804, the LV Ring-Tip column 806, the LV Tip-RV column 808 and the LV Ring-RV column 810. In the illustrated example, column 804 indicates that the PS is present for the LV Tip-Ring pacing vector configuration when the patient is in supine and left recumbent postures and the PS is absent for the same pacing vector configuration when the patient is in standing posture. The illustrated example further shows that column 806 indicates that the PS is present for the LV Ring-Tip pacing vector configuration when the patient is in the standing and left recumbent postures and PS is absent for the same pacing vector configuration when the patient is in the supine posture, column 808 indicates that the patient does not experience PS for the LV Tip-RV pacing vector configuration for any of the tested postures, and column 810 indicates that the PS is present for the LV Ring-RV pacing vector configuration when the patient is in the left recumbent posture and PS is absent for the same configuration when the patient is in the standing and the supine postures.

In an example, the PS search algorithm can include instructions to allow the users such as the physician to define the posture in which to perform the PS search. The user-defined posture for the patient may be listed in a column 802. In an example, the PS search algorithm can include instructions to monitor the sensed posture for posture changes, and conduct a PS search for new or relatively new posture if a relatively recent PS search has not been conducted or if an intervening device event or patient event occurred since the last PS search for that posture. Various criteria for various posture sensors may be implemented to determine "a posture change." By way of example, a three-axis accelerometer may detect the absolute value of the change for each axis (X, Y, Z), and compare a sum of these changes to a threshold value. A posture change may be declared if the sum of the absolute values for the three axes reach or cross the threshold.

Various embodiments may be configured to enable the physician to initiate the PS search when the current posture of the patient matches a desired posture. For example, the device in an ambulatory patient may detect that PS occurs when the patient leans forward, and the physician may attempt to evaluate the patient in a clinical setting by asking the patient to lean forward to recreate the PS events that occurred in the ambulatory setting. As shown, the table 800 may provide an alert message when a current posture of the patient does not match the desired posture. Accordingly, the physician can instruct the patient to move until the current posture of the patient assumes the desired posture for the PS search.

The physician may use the posture data and PS search results for one or more pacing vector configurations to appropriately program the IMD and avoid PS. The PS testing results may indicate that a configuration (e.g. the LV Tip-Ring pacing vector configuration in the example illustrated in FIG. 8) is best suited for the patient due to an absence of PS in any of the determined posture of the patient. Accordingly, the physician can program the IMD to use such a pacing vector configuration to deliver the therapy while avoiding PS. In another example, the physician can use this information to program the IMD to allow the IMD to operate in and switch among any of the listed configurations except for selected pacing vector configuration(s) for selected posture(s) where the prevalence of PS is high.

FIG. 9A illustrates an example of a table 900 listing PS search results for patient postures when the patient is in the ambulatory environment. In an example, the IMD can be configured to execute the PS search algorithm at programmed intervals or upon receiving a request from the patient or upon receipt of a trigger. The IMD can be configured to determine the posture of an ambulatory patient and search for PS for one or more pacing vector configurations when the ambulatory patient is in the posture. The IMD can be configured to store PS search results which can be later retrieved and used by the physician to appropriately program the IMD for avoiding PS.

As shown in the table 900, a column 902 may indicate various postures such as, by way of example and not limitation, sitting, left-recumbent and supine postures for which the PS search algorithm is executed. The column 902 can also indicate other postures such as a posture for which the ambulatory patient may experience PS. A column 904 may be used to indicate the PS search results for the corresponding postures and a column 906 indicates the frequency of occurrence of the PS for the corresponding postures of the patient. In an example, the PS search results recorded in the table 900 depicts that the patient experiences a relatively consistent PS when the patient is in the sitting posture. Also, the IMD identifies that the patient experiences less than 10 PS beats at another particular posture. A PS beat is a pace-induced PS response for a single pace FIG. 9B illustrates a table 920 that indicates PS search results for a number of available pacing vector configurations at enrollment and at particular times after enrollment when the ambulatory patient is in a particular posture. The illustrated table 920, by way of example, lists the PS search results when the ambulatory patient is lying on the patient's left side. The table 920 includes columns for various available pacing vector configurations for which the PS search is conducted. For example, table 920 provides columns for "LV Tip-Ring", "LV Ring-Tip", "LV Tip-RV", and "LV Ring-RV". The rows provide the PS research results for each of the available pacing vector configurations at time periods after implant and when the patient is in the left recumbent posture. For example, the illustrated table 920 includes rows for enrollment (e.g. implant), one month follow-up (1MFU), and 3 month follow-up (3MFU).

Figure 10:
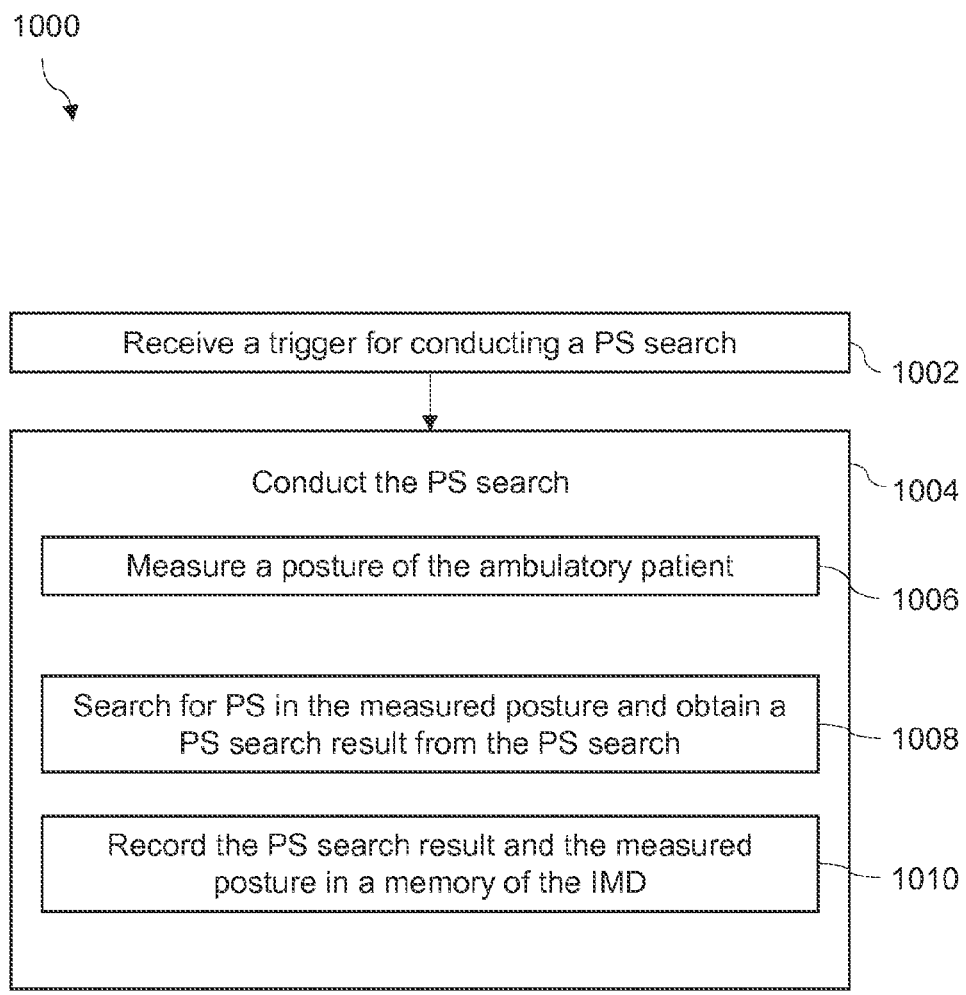
FIG. 10 illustrates, by way of example, an embodiment of a method for conducting a PS search at a posture of the patient.

FIG. 10 illustrates an example of a method 1000 for conducting a PS search. By way of example, the method 1000 can be performed using an IMD implanted within an ambulatory patient. At 1002, a trigger may be received for the IMD to conduct the PS search. The trigger may be an internal trigger activated in response to detection of an event such as a cardiac event, sensor output or other programmable inputs. In another example, the trigger may be an external trigger such as initiated by the physician or the patient to monitor the presence of PS for the particular posture of the patient. At 1004, the PS search may be conducted in response to the trigger. At 1006 the posture of the ambulatory patient may be measured using the implantable posture sensor and at 1008 PS may be searched for the measured posture and a PS search result obtained from the PS search for the measured posture. At 1010 a memory of the IMD may record both the PS search result and the measured posture. In an example, the PS search results and the measured posture may be communicated to an external device such as a programmer that can be configured to display the PS result and the measured posture to the physician or patient.

By way of example, receiving the trigger in the method 1000 can include deriving a posture trigger from an implantable posture sensor. In an example, the posture sensor includes a three-axis accelerometer sensor. An output of a posture sensor may be sampled at programmed regular intervals or programmed irregular intervals to monitor a change in the posture of the ambulatory patient. Deriving the posture trigger may include determining whether a PS search for the measured posture has been recently conducted (e.g. within a programmed time period leading up to a current time), and providing the posture trigger if the programmed time period does not include the PS search. Some embodiments monitor for a change in the posture of the ambulatory patient while conducting the PS search and abort or restart the PS search if it is determined that the posture of the patient has changed from a time when a PS search began. Some embodiments evaluate PS search results and automatically switch a pacing configuration based on the evaluated PS search results.

Figure 11:
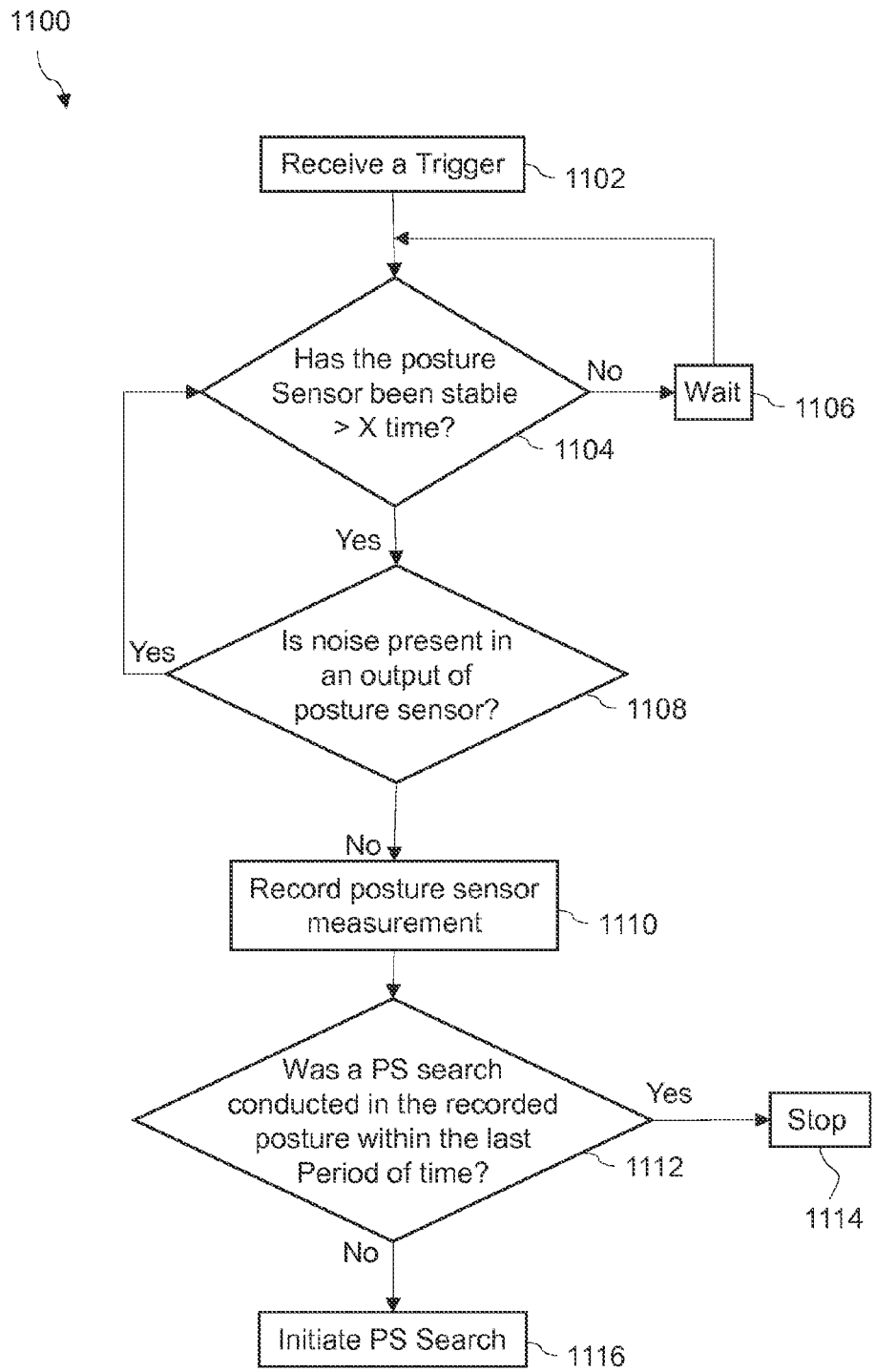
FIG. 11 illustrates, by way of example, an embodiment of a method for initiating a PS search procedure at a posture of the patient.

FIG. 11 illustrates a method 1100 for initiating a PS search at a current posture of the patient. At 1102, a trigger is received to initiate the PS search algorithm. For example, a physician or the patient may intermittently trigger the PS search. In another example, the IMD can be programmed to automatically initiate the PS search procedure on detection of a cardiac event or any other event. In an example, the trigger may be automatically initiated based on a posture change, a change in the patient condition, a change in the device and/or device programming. At 1104, a determination is made as to whether a posture sensor has been stable for a specified amount of time. Thus, PS search routines may not be initiated for transient posture states, but rather only initiated for those positions maintained by the patient for a significant period of time, which may be a programmed value determined by a clinician. The method 1100 can wait for a delay time 1106 if the posture sensor is not found to be stable until the posture sensor is again checked for posture stability. If it is determined that the posture is stable at 1104, the method proceeds to 1108 to determine if too much noise is present in an output signal of the posture sensor. If the output signal is noisy, the method may return back to 1104 to reconfirm that the posture is still stable. If the noise is not found in the output of the posture sensor, the method can proceed to 1110 to record a posture sensor measurement. At 1112, a determination is made as to whether a PS search has been conducted within the last predefined period of time for the recorded posture. By way of example and not limitation, the period of time may be "hours" or "days". The illustrated method proceeds to 1114 if it is determined that the PS search is conducted in the last predefined number of days for the recorded posture and at 1114, the method 1100 can stop. The method may resume, such as if triggered by a posture change or another trigger. The method 1100 can proceed to 1116, if it is determined that the PS search has not been conducted in the last predefined number of days for the recorded posture, to initiate the PS search for one or more pacing configurations and the patient posture. The method may resume, such as if triggered by a posture change or another trigger.

Figure 12:
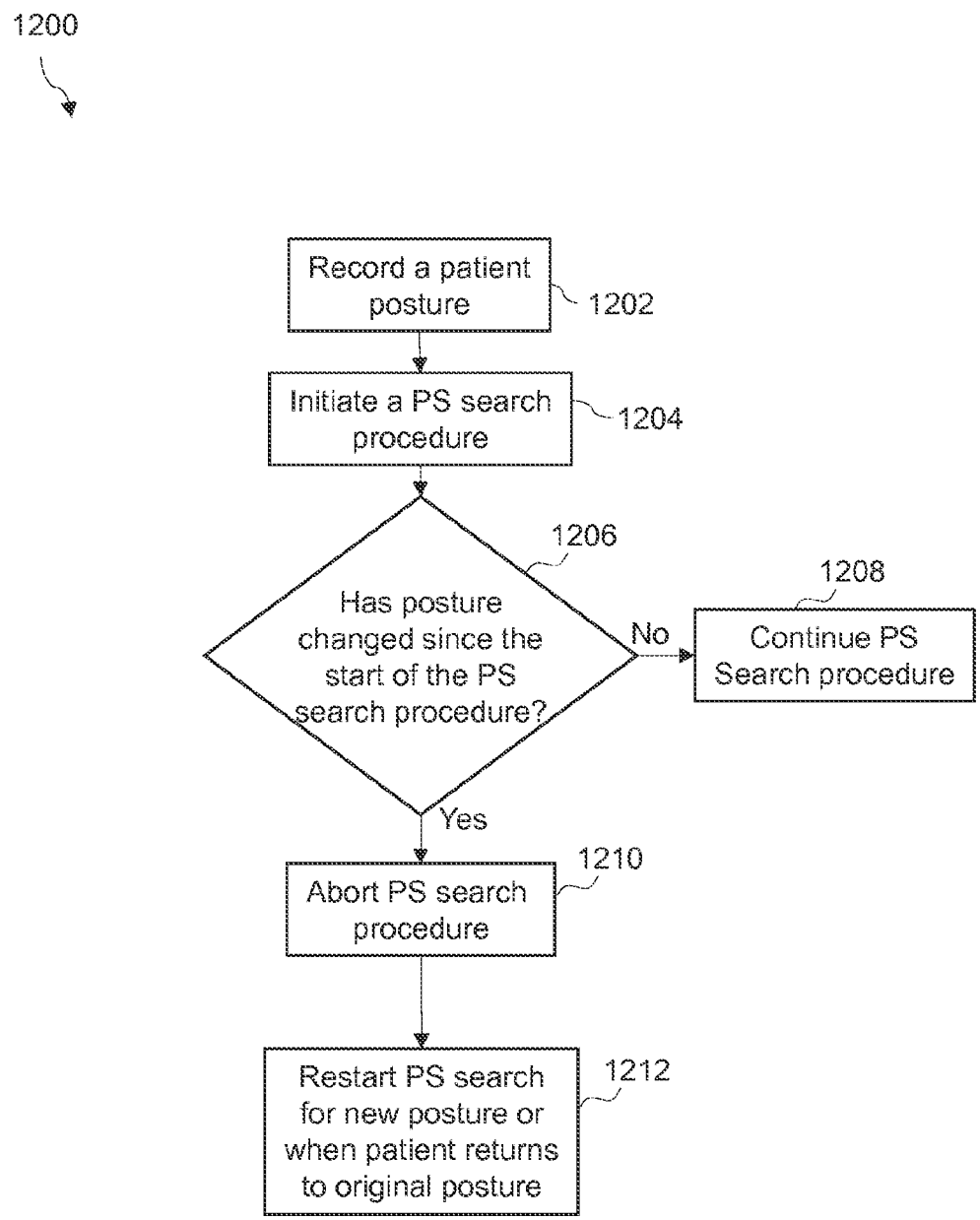
FIG. 12 illustrates, by way of example, an embodiment of a method for aborting a PS search procedure at a posture of the patient.

FIG. 12 illustrates a method 1200 for aborting a PS search procedure because of a posture change. At 1202, a patient posture is recorded. At 1204, a PS search procedure is initiated at the recorded posture of the patient to determine whether PS is present when the patient is at the recorded posture. In an example, each pacing vector configuration available for delivering myocardial stimulation may be tested for PS. At 1206, a determination is made as to whether the posture has changed since the start of the PS search procedure. This determination is made after the PS search has been initiated and before the PS search has been completed. This determination may be made intermittently as long as the PS search continues. The method 1200 can proceed to 1208 to continue the PS search procedure if it is determined that there is no change in the posture since the start of the PS search procedure. The method 1200 can proceed to 1210 if it is determined that the posture has changed since the start of the PS search procedure, and at 1210 the PS search procedure is aborted as the patient has moved from the patient's position when the PS search procedure was initiated. At 1212, the PS search procedure is restarted to provide a PS search for the new posture of the patient or may be restarted when the patient returns to the original posture.

Figure 13:
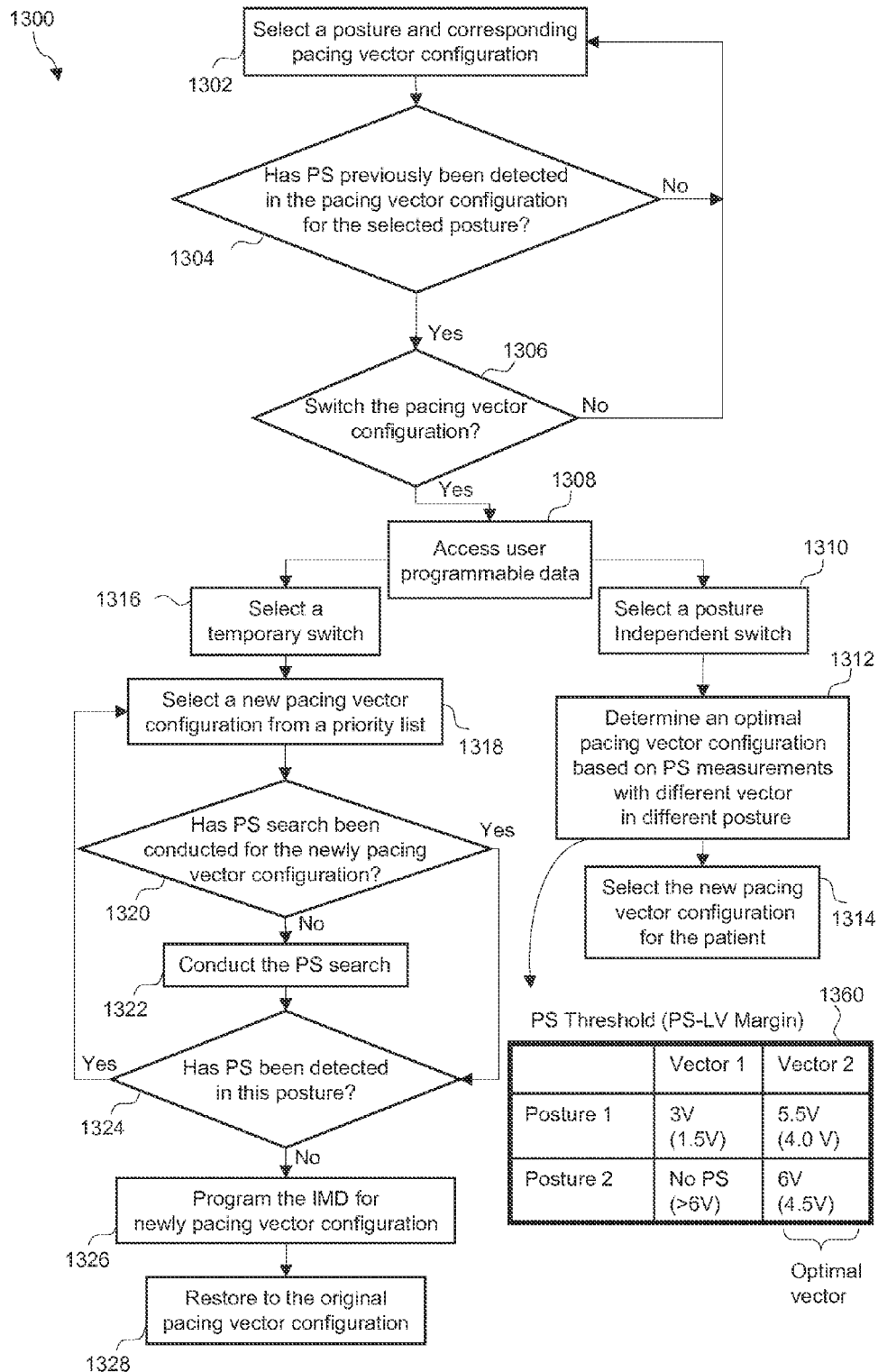
FIG. 13 illustrates, by way of example, an embodiment of a method for selecting a pacing vector for avoiding PS for a posture of the patient.

FIG. 13 illustrates a method 1300 for selecting a pacing vector configuration for avoiding PS for a posture of the patient. At 1302, a posture and a corresponding pacing vector configuration are selected and at 1304 a determination is made as to whether PS has been previously detected in the selected pacing vector configuration and selected posture. The method 1300 can return to 1302 if it is determined that the PS has not been previously detected, and another pacing vector configuration and posture combination can be selected. If it is determined that PS has been detected previously in the selected pacing vector configuration and posture, a determination is made, as illustrated at 1306, as to whether the pacing vector configuration should be switched for the selected posture of the patient. In an example, the determination of switching of the pacing vector configuration can depend on severity or frequency of PS for the selected pacing vector configuration. For example, a higher frequency of PS for the selected pacing vector configuration can cause discomfort to the patient and can lead to the determination of switching the pacing vector configuration to another pacing vector that can exhibit a relatively lesser or zero frequency of occurrence of PS for the selected posture of the patient. The method 1300 can return to 1302 if the pacing vector configuration does not need to be switched, and another pacing vector configuration and posture combination can be selected. If the pacing vector should be switched at 1306, the method can proceed to 1308 to access user programmable data. In an example, the user programmable data can include conditions, events, protocols or other information based on which the pacing vector configuration can be switched to another pacing vector using a long term switch or a temporary switch. The user programmable data may be a preferred vector set by the user or a hemodynamically optimal vector. For example, the user can program the IMD to switch the pacing vector configuration for the selected posture to another pacing vector configuration upon determining that the pacing vector configuration of the selected posture has a relatively severe occurrence of PS for the selected and other different postures of the patient. The switch to a new pacing vector configuration may be a temporary switch based on the currently-detected posture or may be a longer-term switch based on more than one posture over a longer period of time. At 1310, a posture independent switch is selected. Thus, rather than switching pacing vectors based on posture, the system may be configured to determine an optimal pacing vector configuration at 1312 based on PS measurements for different pacing vector configurations corresponding to different postures of the patient. At 1314, the optimal pacing vector configuration is selected for the patient such as to avoid presence of the unintended PS for the selected and other postures of the patient. As illustrated in FIG. 13, a table 1360 indicates values associated with PS threshold and PS-LV margins for different pacing vector configurations such as a vector 1 and a vector 2 at corresponding postures such as at a posture 1 and a posture 2. A PS-LV margin may represent the difference between the highest pacing pulse amplitude that does not cause PS and the lowest pacing pulse that captures LV. Based on an analysis of the PS threshold and PS-LV margin values, it can be determined that vector 2 maintains a relatively similar PS-LV margins across the posture 1 and posture 2 and can be considered as an optimal pacing vector for the patient for avoiding PS across both of the postures 1 and 2. The selection of the long-term switch can enable the physician to program the IMD to select an optimal pacing vector configuration for a number of different postures.

At 1316, the method 1300 can include selection of the temporary switch that can switch the pacing vector configuration of the selected posture to another pacing vector configuration until the posture is switched again. At 1318, a new pacing vector configuration available on a priority list is selected for the posture of the patient. The priority list can include one or more pacing vector configurations and corresponding ranks for the pacing vector configurations. In an example, the pacing vector configurations can be ranked based on one or more of the values of the hemodynamic function parameter, the cardiac capture threshold and the PS threshold. For example, a pacing vector configuration having the highest PS threshold value can have the highest rank in the priority list. At 1320, a determination is made as to whether a PS search has been previously conducted for the newly selected pacing vector configuration. The method 1300 can proceed to 1322 if the PS search has not been previously conducted for the newly selected pacing vector configuration, and at 1322 a PS search procedure is conducted for the newly selected pacing vector configuration. The method 1300 can proceed to 1324 if PS search has been previously conducted for the newly selected pacing vector configuration.

At 1324, a determination is made as to whether PS has been previously detected in the newly selected pacing vector configuration for the selected posture of the patient. The method 1300 can proceed to 1318 if PS has been previously detected in the newly selected pacing vector configuration, and at 1318 another pacing vector configuration can be selected depending on the rank associated with the another pacing vector configuration. The method 1300 can proceed to 1326 if it is determined that no PS has been previously detected in the newly selected pacing vector configuration. At 1326, the IMD can be programmed for the newly selected pacing vector configuration such as to avoid the presence of unintended PS for the selected posture of the patient. At 1328, the original pacing vector configuration is restored when the patient moves out of the selected posture. That is to say, the temporary switch allows the newly selected pacing vector configuration to be activated only for the period the patient is in the selected posture. As the patient moves out of this posture, the IMD can be reprogrammed to switch to the original pacing vector configuration.

As will be understood by those of ordinary skill in the art, at least part of the processes may be implemented using a machine or computer, using instructions encoded on a machine-readable or computer-readable medium.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method performed using an implantable medical device (IMD) within a patient, the method comprising:
    receiving a trigger for conducting a pace-induced phrenic nerve stimulation (PS) search using the IMD within an ambulatory patient, wherein receiving the trigger includes deriving a posture trigger from the implantable posture sensor, wherein deriving the posture trigger includes searching for a recently-conducted PS search for the measured posture within a programmed time period leading up to a current time, and providing the posture trigger if the programmed time period does not include the PS search;
    in response to the trigger, conducting the PS search using the IMD, wherein conducting the PS search includes:
        measuring a posture of the patient using an implantable posture sensor;
        searching for PS while the patient is in the measured posture and obtaining a PS search result from the PS search for the measured posture; and
        recording in a memory of the IMD both the PS search result and the measured posture.

2. The method of claim 1, wherein the IMD is configured with more than one pacing configuration, wherein searching for PS includes searching for PS for each of the more than one pacing configurations while the patient is in the measured posture, and recording includes recording in the memory the PS result for each of the more than one pacing configurations.

3. The method of claim 2, wherein recording in the memory includes recording the PS result for each of the more than one pacing configurations at more than one time period after implant.

4. The method of claim 1, further comprising determining if there is a posture change during the PS search for the measured posture, and aborting the PS search for the measured posture.

5. The method of claim 4, further comprising measuring a new posture resulting from the posture change and beginning a PS search for the new posture.

6. The method of claim 4, further comprising determining that the patient returned to the measured posture, and restarting the PS search for the measured posture.

7. The method of claim 1, wherein the IMD is configured with more than one pacing configuration for pacing the patient, the method further comprising evaluating a detected PS event and automatically switching the pacing configuration from a first pacing configuration to a second pacing configuration based on the evaluated detected PS event and previous search results for the second pacing configuration.

8. The method of claim 7, wherein evaluating the detected PS event includes detecting a changed patient posture corresponding to the detected PS event, and automatically switching the pacing configuration includes switching the pacing configuration to another pacing configuration until the patient moves out of the changed patient posture.

9. The method of claim 1, wherein the trigger includes an external trigger signal.

10. The method of claim 1, wherein implantable posture sensor includes a three-axis accelerometer.

11. The method of claim 1, further comprising communicating the PS result and the measured posture to an external device, wherein the external device is configured to display the PS result and the measured posture.

12. A system, comprising:
    an implantable medical device (IMD) for implantation in a patient, the IMD including:
        a posture sensor;
        a pace-induced phrenic nerve stimulation (PS) sensor;
        a memory; and
        a controller, wherein the controller is operably connected to the posture sensor to detect posture and the PS sensor to detect phrenic nerve stimulation;
    wherein the controller is configured to:
        receive a trigger for conducting a PS search, wherein the trigger includes a posture trigger, and the controller is configured to derive the posture trigger from the posture sensor;
        conduct the PS search in response to the trigger, wherein the PS search conducted by the controller includes:
            measuring a posture of the patient using the posture sensor;
            searching for PS using the PS sensor while the patient is in the measured posture and obtaining a PS result from the PS search for the measured posture; and
            recording in the memory both the PS result and the measured posture,
    wherein the controller is configured to determine if a PS search was successfully conducted for the measured posture within a programmed time period leading up to a current time, and to provide the posture trigger if the PS search was not conducted within the programmed time period.

13. The system of claim 12, wherein the system is configured to pace in more than one pacing configuration, wherein the controller is configured to search for PS for each of the more than one pacing configurations while the patient is in the measured posture, and record in the memory the PS result for each of the more than one pacing configurations.

14. The system of claim 13, wherein the controller is configured to record in memory the PS result for each of the more than one pacing configurations at more than one time period after implant.

15. The system of claim 12, further wherein the controller is configured to use the posture sensor to detect a posture change during the PS search for the measured posture, and to abort or restart the PS search for the detected posture change.

16. The system of claim 12, wherein:
the controller is configured with a pacing configuration for generating paces; and
the controller is configured to:
detect a PS using the PS detector;
perform an evaluation of the detected PS; and
automatically switch the pacing configuration based on the evaluation.

17. The system of claim 16, wherein in performing the evaluation the controller is configured to detect a changed patient posture, and switch the pacing configuration to another pacing configuration until the patient moves out of the changed patient posture.

18. The system of claim 12, further comprising:
an external device, wherein the IMD and the external device are configured to communicate,
wherein the IMD is configured to:
conduct a plurality of PS searches, including at least one PS search for each one of a number of different measured postures, wherein the number includes at least two different measured postures; and
for each one of the measured postures record in the memory the PS result and the measured posture; and
communicate the PS result and the measured posture to the external device, the external device including a display, and
wherein the external device includes a display and is configured to present on the display the PS result and the measured posture for each one of the measured postures.

19. The system of claim 12, wherein the posture sensor includes an accelerometer.

20. The system of claim 12, wherein the PS detector includes an accelerometer.

* * * * *